US010918402B2

(12) United States Patent
Chu

(10) Patent No.: US 10,918,402 B2
(45) Date of Patent: Feb. 16, 2021

(54) MEDICAL DEVICE HANDLES AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 279 days.

(21) Appl. No.: 15/872,091

(22) Filed: Jan. 16, 2018

(65) Prior Publication Data

US 2018/0206863 A1  Jul. 26, 2018

Related U.S. Application Data

(60) Provisional application No. 62/449,150, filed on Jan. 23, 2017.

(51) Int. Cl.
A61B 17/221 (2006.01)
A61B 90/50 (2016.01)
A61B 1/00 (2006.01)
A61B 17/29 (2006.01)
A61B 1/018 (2006.01)
A61B 17/00 (2006.01)

(52) U.S. Cl.
CPC .......... A61B 17/221 (2013.01); A61B 1/0014 (2013.01); A61B 1/00066 (2013.01); A61B 1/00133 (2013.01); A61B 1/018 (2013.01); A61B 17/2909 (2013.01); A61B 90/50 (2016.02); A61B 17/00234 (2013.01); A61B 2017/00367 (2013.01); A61B 2017/00477 (2013.01); A61B 2017/2215 (2013.01); A61B 2017/2927 (2013.01)

(58) Field of Classification Search
CPC . A61B 17/22; A61B 17/221; A61B 17/22004; A61B 17/32056; A61B 17/00234; A61B 2017/2215; A61B 2017/2212
See application file for complete search history.

(56) References Cited

U.S. PATENT DOCUMENTS

2004/0015050 A1* 1/2004 Goto .................. A61B 18/1492 600/104
2006/0247494 A1* 11/2006 Nakagawa ......... A61B 18/1492 600/104
2014/0171833 A1 6/2014 Matsuno et al.

FOREIGN PATENT DOCUMENTS

EP 1502537 A1 2/2005

OTHER PUBLICATIONS

International Search Report and Written Opinion in PCT/US2018/013772, dated Apr. 26, 2018 (12 pages).

* cited by examiner

Primary Examiner — Vi X Nguyen
(74) Attorney, Agent, or Firm — Bookoff McAndrews, PLLC

(57) ABSTRACT

An insertion device includes a body and a delivery shaft, and the body includes a longitudinal axis aligned with a central long axis of a proximal end of the delivery shaft. A holder may be coupled to the body of the insertion device, and the holder includes a medical device receiving chamber having a longitudinal axis that is non-parallel to the longitudinal axis of the body.

14 Claims, 10 Drawing Sheets

MEDICAL DEVICE HANDLES AND RELATED METHODS

CROSS-REFERENCE TO RELATED APPLICATIONS

This patent application claims the benefit of priority under 35 U.S.C. § 119 to U.S. Provisional Patent Application No. 62/449,150, filed Jan. 23, 2017, which is herein incorporated by reference in its entirety.

TECHNICAL FIELD

Various aspects of the present disclosure relate generally to medical devices. More specifically, the present disclosure relates to medical devices and attaching configurations for medical devices.

BACKGROUND

Medical devices, such as expandable baskets, retrieval devices, and the like may include a shaft, and may be arranged for delivery through a working channel of an insertion device (e.g., an endoscope). The shaft of such medical devices may be selectively extended and retracted relative to the distal end of the working channel of the insertion device or a sheath of the device to deploy or retract the shaft to perform one or more therapies, treatments, or diagnostic evaluations on a subject. For example, the medical device may include a shaft that terminates distally at an end effector such as an expandable basket. However, extending and retracting the end effector while coupled to an endoscope may require difficult or complex hand manipulations, or multiple users to hold separate components. The devices and methods of the current disclosure may rectify some of the deficiencies described above and/or address other aspects of the prior art.

SUMMARY

Examples of the present disclosure relate to, among other things, medical devices. Each of the examples disclosed herein may include one or more of the features described in connection with any of the other disclosed examples.

In one example, an insertion device may include a body and a delivery shaft, wherein the body includes a longitudinal axis aligned with a central long axis of a proximal end of the delivery shaft; and a holder coupled to the body of the insertion device, wherein the holder includes a medical device receiving chamber having a longitudinal axis that is non-parallel to the longitudinal axis of the body.

The insertion device may further include one or more of the following features. The medical device receiving chamber may have a semi-circular shape and be located at a top portion of the holder. The holder may further include a stop surface forming an extension of the handle chamber. The stop surface may have a semi-circular shape that is aligned with the semi-circular shape of the receiving chamber. The stop surface may be narrower and/or shallower than the medical device receiving chamber.

The insertion device may further include an attachment surface. The holder may further include a finger ridge opposite the attachment surface. The attachment surface may be coupled to a rounded portion of the body. The attachment surface may include slots, shallow grooves, or projections. The holder may be coupled to a proximal portion of the body. The insertion device may further include a deflection lever to deflect a distal end of the delivery shaft, and the holder may be coupled to the body of the insertion device on a side opposite to the deflection lever The insertion device may further comprise a medical device coupled to the insertion device via the holder. The medical device may include a shaft, and the shaft may be introduced into the delivery shaft. The chamber of the holder may comprise a female connector and further include an alignment groove. The body of the insertion device may include holes, and the holder may further include a distal extension and holder pins to fit within the insertion device holes to assist in coupling the holder to the insertion device. A medical device may be coupled to the insertion device via the holder, and the medical device may include a male connector and an alignment pin.

In another example, an insertion device may include a body and a delivery shaft extending from the body, and a medical device holder coupled to one of the body or the delivery shaft. The medical device holder may include a handle chamber and a stop surface having an edge facing the handle chamber.

The insertion device may further include one or more of the following features. The medical device holder may further include an attachment surface, and the attachment surface may be coupled to a proximal portion of the body. The holder may further include at least two legs, each having a through-hole. The holder may be coupled to the delivery shaft with the delivery shaft axially passing through the through-holes in the at least two legs.

In another example, an insertion device may include a body having a distal portion, an intermediate portion, and a proximal portion, a delivery shaft extending from the distal portion, a deflection lever on the proximal portion to deflect a distal end of the delivery shaft, and a medical device holder coupled to the proximal portion. The medical device holder may be coupled to the proximal portion of the body on a side opposite the deflection lever. The insertion device may further include a medical device coupled to the medical device holder, and the medical device may include a handle, a plunger, and a shaft coupled to a distal end of the plunger.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical device holders for coupling a medical device to an insertion device to deploy a shaft from the medical device. The medical device may include any type of end effector or retrieval device, such as, e.g., an expandable retrieval basket.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figure 1:
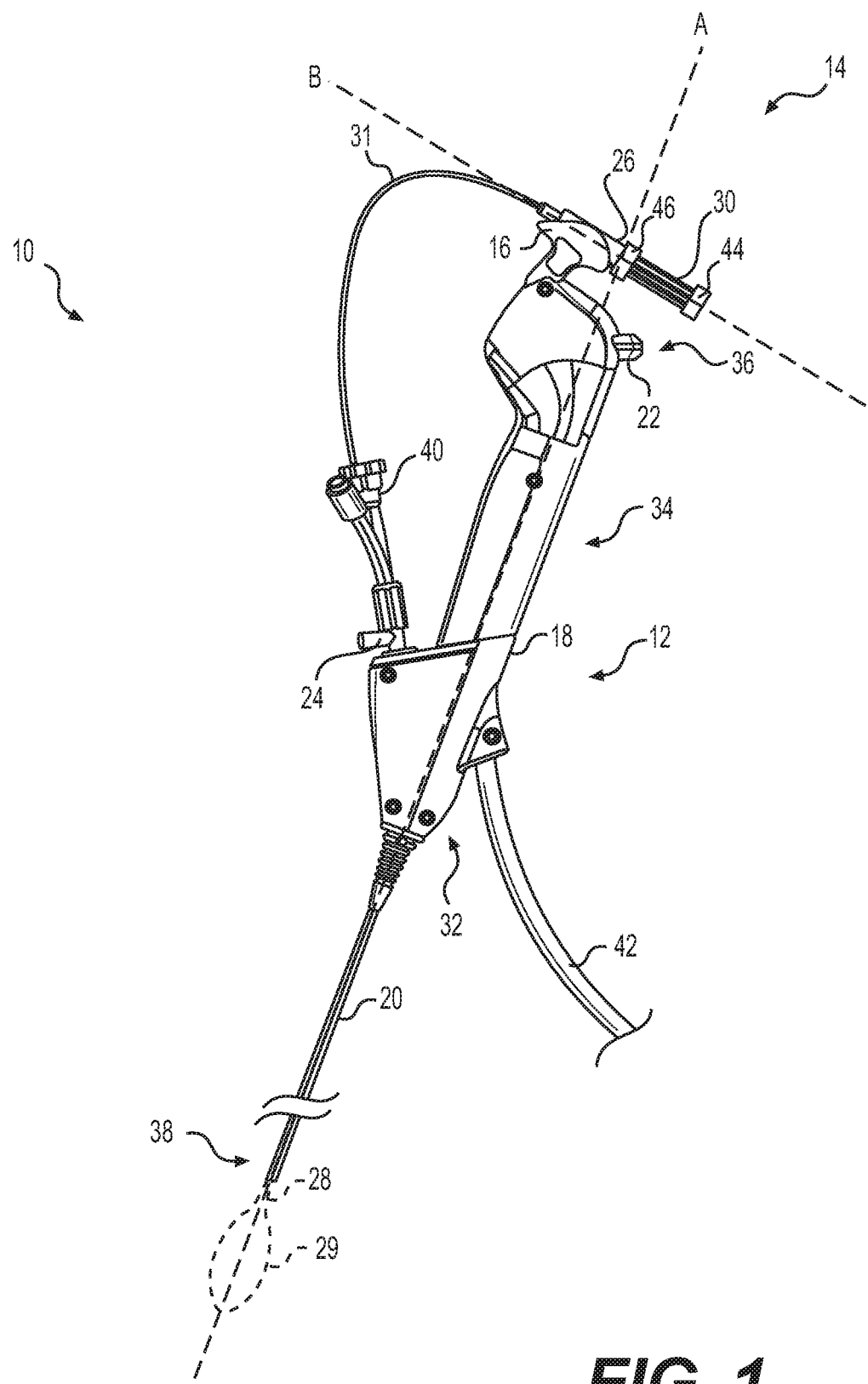
FIG. 1 illustrates a medical device coupled to an insertion device via an exemplary holder.

FIG. 1 illustrates a medical system 10, including an insertion device 12, a medical device 14, and a holder 16. Insertion device 12 may include a body 18 and a delivery shaft 20, with the body 18 including a deflection lever 22 and at least one port 24. Medical device 14 may include a handle 26, a shaft 28, end effector 29, and an actuator or plunger 30. Shaft 28 is at least partially surrounded by a sheath 31 Holder 16 may be coupled to the insertion device 12 such that medical device 14 may be mounted in holder 16 proximate to deflection lever 22.

Insertion device 12 may be a ureteroscope (e.g., Lithovue™ Single-Use Digital Flexible Ureteroscope by Boston Scientific Corp.), an endoscope, a hysteroscope, a bronchoscope, a cystoscope, or any similar device. Insertion device 12 may be for single-use and be disposable, or insertion device 12 may be reusable. The body 18 of insertion device 12 may have a distal portion 32, an intermediate portion 34, and a proximal portion 36. Body 18 has a longitudinal axis A aligned with a central long axis of a proximal end of the delivery shaft 20. The deflection lever 22 may be positioned on a rounded corner of the proximal portion 36 and be manipulated to deflect a distal end 38 of the delivery shaft 20. The intermediate portion 34 may be generally a constant diameter, and may form a portion of the insertion device 12 that a user may grip such that the user's thumb is proximate the deflection lever 22. The at least one port 24 may be positioned in the distal portion 32. The at least one port 24 may be a T-connector as shown in FIG. 1, may be a Y-connector, or another appropriate connector. Port 24 may be threaded or may be a luer component. The at least one port 24 may connect to the delivery shaft 20 through at least one internal lumen (not shown) in the body 18 of insertion device 12. Additionally, a fitting 40 may be coupled to the at least one port 24, such as, for example, a gateway fitting, that may form a seal over port 24. Though not shown, insertion device 12 may include an integral camera at the distal end 38 that is connected to processing software and a display via a communication and power conduit 42.

Medical device 14 will be described as a retrieval basket device; however, it is understood that medical device 14 may be any type of medical device used in conjunction with insertion device 12 to delivery medical therapy to a target site inside a subject. For example, medical device 14 may alternatively be a laser fiber, an irrigation and/or aspiration tube, a snare, forceps, and/or a needle.

Shaft 28 of medical device 14 may be movable to extend or retract an end effector at a distal end of shaft 28. Shaft 28 may be coupled to a distal end of plunger 30, such that movement of plunger 30 relative to handle 26 extends or retracts the shaft 28. Alternatively, shaft 28 may be coupled to a proximal portion of plunger 30, or shaft 28 and/or a shaft connector (not shown) may extend proximally beyond a proximal end of plunger 30 to allow user manipulation, for example, to connect a laser fiber or irrigation and/or aspiration tube to an external source. Plunger 30 may further include a plunger knob 44 at a proximal end of plunger 30 to aid in manipulation by, for example, a user's fingers. Plunger 30 may be movable through an axial lumen in handle 26, and the movement of plunger 30 through handle 26 may further be biased by a biasing member (not shown), such as, for example, a spiral (compression) spring. Handle 26 may also include a handle knob 46 at a proximal end of handle 26 to aid in manipulation by, for example, a user's fingers. In a non-illustrated example, plunger 30 may include at least one plunger pin and handle 26 may include at least one pin-receiving slot, such that axial and rotational movement of the plunger 30 relative to handle 26 is limited or locked by the movement of the at least one plunger pin within the at least one pin-receiving slot.

Shaft 28 is at least partially surrounded by sheath 31, and sheath 31 may be coupled to the handle 26, for example, at the distal end of handle 26, such that movement of plunger 30 relative to handle 26 causes shaft 28 to move relative to the sheath 31. Shaft 28, with sheath 31, may be inserted through fitting 40 and/or port 24.

As shown in FIG. 1, holder 16 may be coupled to insertion device 12, and medical device 14 may be mounted in holder 16. Holder 16 may be positioned on the proximal portion 36 of insertion device 12 on a corner opposite to the deflection lever 22. Holder 16 may be permanently attached via adhesive, screws, or another fastener. Holder 16 may also be removably attached via straps, tape, Velcro®, clamps, snaps, or the like. Holder 16 may also be molded to the insertion device 12, or may be integrally formed with the insertion device 12.

In one aspect, when medical device 14 is mounted in holder 16, plunger 30 may be positioned proximate to deflection lever 22. Additionally, shaft 28 and sheath 31 may have lengths such that when mounted in holder 16, distal ends of shaft 28 and sheath 31 are flush with or just proximal to the distal end 38 of delivery shaft 20. As such, a pushing action on plunger 30 serves to extend the distal end of shaft 28 distally out of sheath 31 and from the distal end 38 of delivery shaft 20. In another aspect, shaft 28 and sheath 31 may have lengths such that when mounted in holder 16, distal ends of shaft 28 and sheath 31 extend distally beyond the distal end 38 of delivery shaft 20. As such, the shaft 28 and sheath 31 may extend beyond the delivery shaft 20 to reach a target material. Additionally, a user may adjust the distance the shaft 28 and sheath 31 extend beyond the distal end 38 by adjusting the portions of the shaft 28 and sheath 31 that are proximal to fitting 40.

Figure 2:
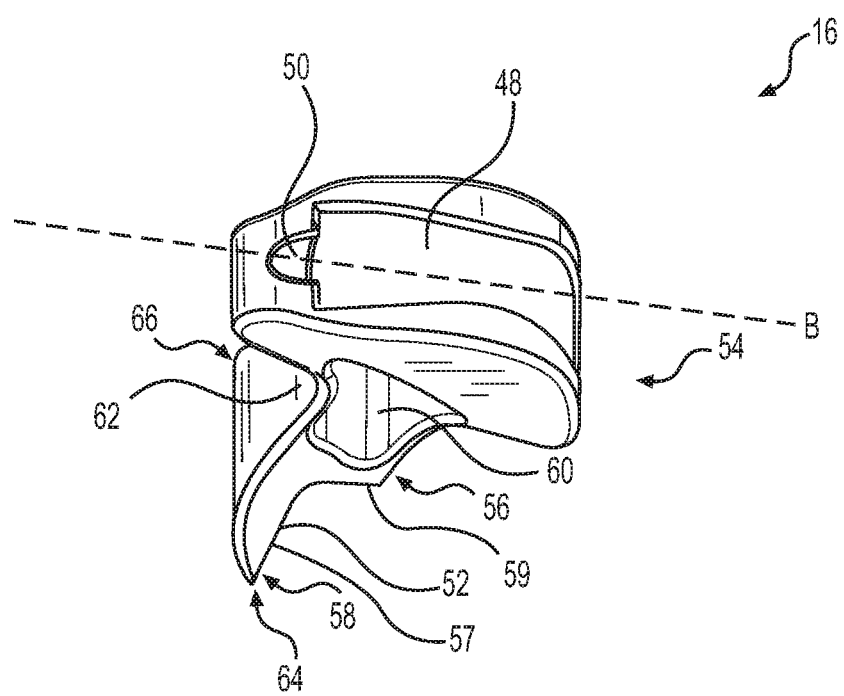
FIG. 2 illustrates a perspective view of the exemplary holder of FIG. 1.

As shown in FIG. 2, holder 16 includes a handle chamber 48, a stop surface 50, and an attachment surface 52. Handle chamber 48 may receive a medical device by mating or engaging with an outer surface of the handle 26 of the medical device 14. Handle chamber 48 may have a semi-circular shape and may be located at a rounded top portion 54 of holder 16. Handle chamber 48 may include a longitudinal axis B that is non-parallel to the longitudinal axis A of the body 18 of the insertion device 12 (FIG. 1). Stop surface 50 may also have a semi-circular shape and may be located at the top portion 54, with the stop surface 50 being narrower and shallower than handle chamber 48. Stop surface 50 may form an extension of a forward edge of handle chamber 48 and may accommodate a distal tip of handle 26 that is smaller in size than a main body portion of handle 26 of the medical device 14. The semi-circular shape of stop surface 50 may be aligned with the semi-circular shape of the handle chamber 48. Stop surface 50 may stabilize the handle 26 during movement of plunger 30. Top portion 54 may be wider than a middle portion 56 and a bottom portion 58. Middle portion 56 may include a through-hole 60. Attachment surface 52 may be shaped to match the portion of the insertion device 12 to which holder 16 is mounted. In one example illustrated in FIG. 2, attachment surface 52 includes a flat bottom portion 57 and a curved top portion 59 such that attachment surface 52 may match the curve of the proximal portion 36 of insertion device 12. A side of bottom portion 58 opposite to attachment surface 52 may have a curved bottom portion, a generally flat middle portion, and an outwardly curved top portion to form a finger ridge 62.

Attachment surface 52 may include additional components such that holder 16 may be coupled to insertion device 14. For example, attachment surface 52 may include slots for screws, straps, or other aforementioned fasteners. Attachment surface 52 may also be flat or include shallow grooves such that holder 16 may be glued to insertion device 12. In another embodiment, attachment surface 52 may include extensions or prongs at a front end 64 and a back end 66 such that holder 16 may snap on to, slide into, or otherwise attach to insertion device 12 between the extensions or prongs.

In use, delivery shaft 20 of insertion device 12 may be inserted into a subject to a surgical site. Holder 16 may be coupled to insertion device 12 before the insertion, or holder 16 may be coupled to insertion device 12 after insertion. Medical device 14 may then be inserted into insertion device 12 through port 24, with or without fitting 40, such that shaft 28 and sheath 31 are just proximal, flush with, or extend distally beyond distal end 38 of delivery shaft 20. Shaft 28 and sheath 31 may be introduced into insertion device 12 using an introducer sheath (not shown) to rapidly introduce the shaft into port 24. Medical device 14 may be coupled to insertion device 12 by handle 26 fitting in holder 16.

Movement of deflection lever 22 deflects distal end 38 of delivery shaft 20 to be proximate to the surgical site. Then, because medical device 14 is positioned proximate to deflection lever 22, a user may easily extend and/or rotate shaft 28 through action on plunger 30 and plunger knob 44 to deliver medical treatment. After delivering medical treatment, the plunger 30 may be retracted proximally to retract shaft 28 and sheath 31 within distal end 38 of delivery shaft 20. As mentioned, a biasing member enclosed within handle 26 may bias plunger 30 to return proximally. The deflection and extension steps may be repeated if, for example, there are multiple surgical sites or the target tissue moves, or the medical device 14 and insertion device 12 may be removed from the subject. Alternatively, medical device 14 may be removed from insertion device 12, and an additional medical device may be inserted into insertion device 12 and coupled via holder 16 to deliver further medical treatment. Furthermore, if holder 16 is removably coupled to insertion device 12, holder 16 may be uncoupled from insertion device 12, and a different holder may be coupled to insertion device 12 to accommodate a different medical device.

Figure 3:
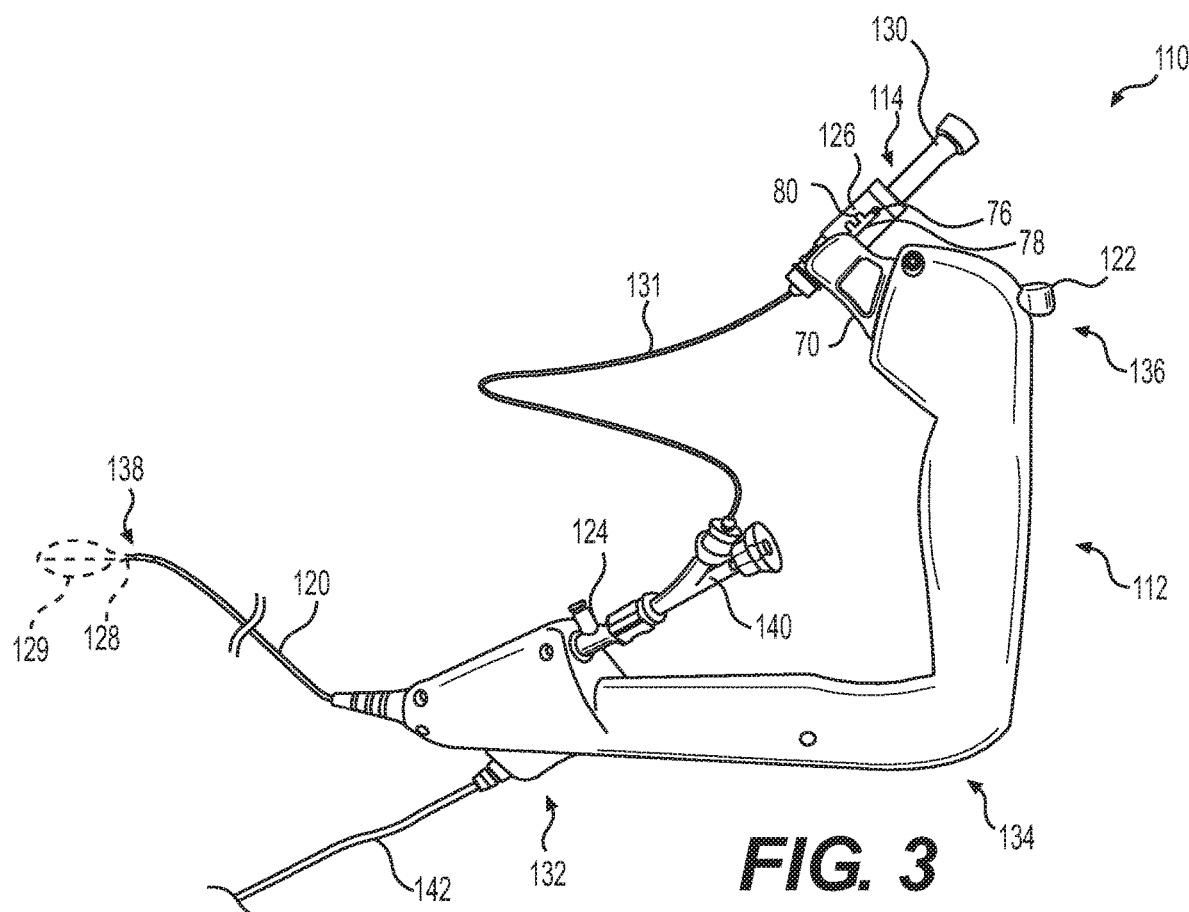
FIG. 3 illustrates a medical device coupled to an insertion device via an alternative holder according to aspects of this disclosure.

FIG. 3 illustrates another aspect of the disclosure with similar elements to the medical system 10 shown by 100 added to the reference numbers. Medical system 110 includes insertion device 112, which may be an L-shaped insertion device 112 with similar functioning to the insertion device 12 of FIG. 1, including delivery shaft 120, deflection lever 122, port 124, and communication and power conduit 142. Like the previous example, medical device 114 may be inserted into insertion device 112 through port 124, with or without a fitting 140, such that shaft 128 and sheath 131 are proximate to or flush with distal end 138 of the delivery shaft 120.

Medical device 114 may be coupled to insertion device 112 via a holder 70 in a similar manner as discussed with respect to FIG. 1, and may be positioned on the proximal portion 136 of insertion device 112 on a corner opposite to the deflection lever 122. As with FIG. 1, when medical device 114 is mounted in holder 70, plunger 130 may be positioned proximate to deflection lever 122. Shaft 128, with end effector 129, and sheath 131 may have lengths such that when mounted in holder 70, distal ends of shaft 128 and sheath 131 are flush with, just proximal to, or extend distally beyond the distal end 138 of delivery shaft 120. As such, pushing plunger 130 serves to extend the distal end of shaft 128 distally out of sheath 131 and from the distal end 138 of delivery shaft 120.

Figure 4:
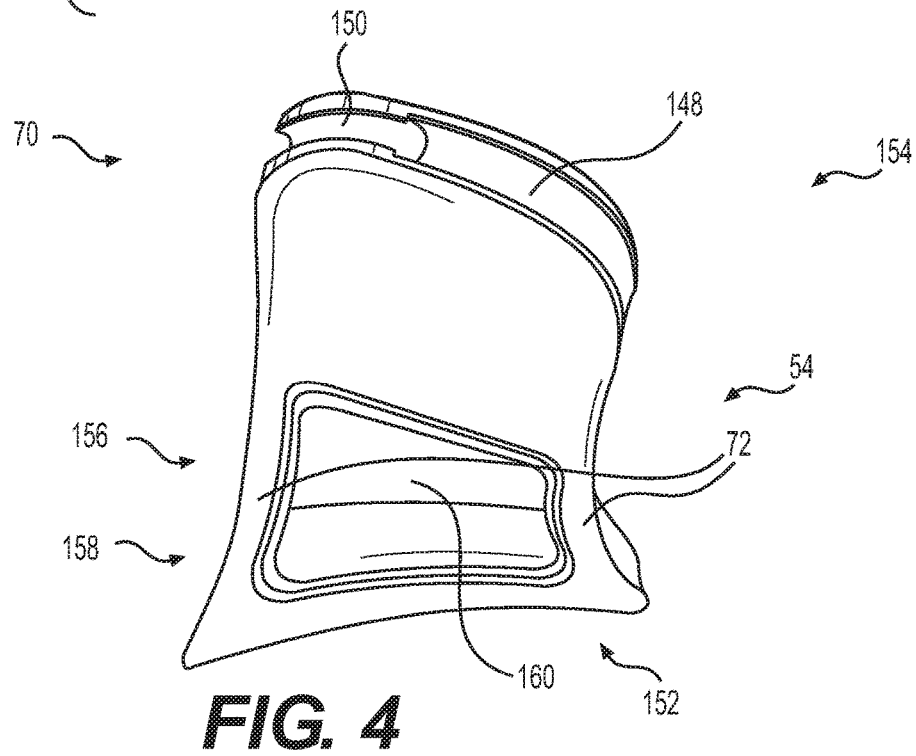
FIG. 4 illustrates a perspective view of the holder of FIG. 3

As shown in FIG. 4, holder 70 includes a handle chamber 148, a stop surface 150, and an attachment surface 152. Handle chamber 148 may mate or engage with an outer surface of the handle 126 of the medical device 114. Handle chamber 148 may be a semi-circular cutout from a rounded top portion 154 of holder 70. Stop surface 150 may be a semi-circular cutout from the top portion 154, with the stop surface 150 being narrower and shallower than handle chamber 148. Stop surface 150 may extend from a forward edge of handle chamber 148 and may accommodate a distal tip or portion of handle 126 that is smaller in size than a main body portion of handle 126 of the medical device 114. Stop surface 150 may stabilize the handle 126 during movement of plunger 130. Top portion 154 may be wider than a middle portion 156 and a bottom portion 158. Middle portion 156 may include a through-hole 160 and two supports 72 connecting attachment surface 152 to handle chamber 148. Attachment surface 152 may also be shaped to match the portion of the insertion device 112 to which holder 70 is mounted. In one example illustrated in FIG. 4, attachment surface 152 includes a generally flat bottom portion such that attachment surface 152 may match the shape of the proximal portion 136 of insertion device 112.

Attachment surface 152 may include additional components such that holder 70 may be coupled to insertion device 112 as discussed with respect to holder 16.

As shown in FIG. 3, medical device 114 may include a handle 126, a shaft 128, a plunger 130, and a sheath 131 and may function in a similar manner to medical device 114 as discussed above. Sheath 131 at least partially surrounds shaft 128 and may be coupled to a distal end of the handle 126. In one aspect, plunger 130 may include a pin 76, and handle 126 may include a track 78 with at least one tab 80, such that plunger 130 may be lockably positioned within handle 126. The portions of shaft 128 and sheath 131 proximal to fitting 140 may determine the position of the shaft 128 and sheath 131 relative to the distal end 138 of the insertion device 112. In this aspect, the position of the plunger 130 relative to the handle 126 may determine the position of the shaft 128 relative to the sheath 131. As such, a user may deflect the distal end 138 of the insertion device 112 via deflection lever 122 and extend and/or rotate shaft 128 simultaneously using only two hands.

Figure 5:
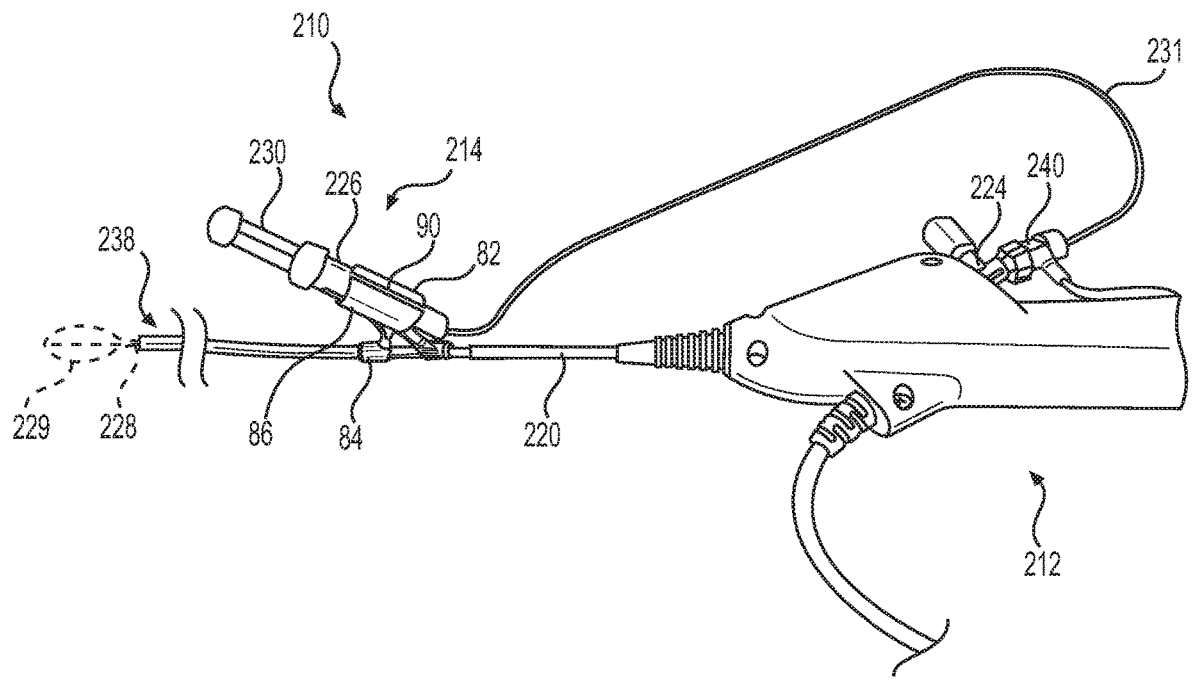
FIG. 5 illustrates a medical device coupled to an insertion device via an alternative holder according to aspects of this disclosure.
Figure 6:
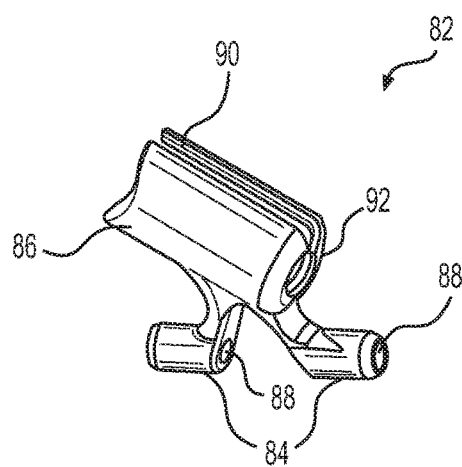
FIG. 6 illustrates a perspective view of the holder of FIG. 5.

FIGS. 5 and 6 illustrate another embodiment of the disclosure with similar elements to the medical system 10 shown by 200 added to the reference numbers. The medical system 210 of FIG. 5 includes insertion device 212 and medical device 214 similar to that of FIG. 1. FIG. 5 also includes holder 82 to couple medical device 214 to insertion device 212.

As shown in FIG. 6, holder 82 includes at least two legs 84 and a holder body 86. Legs 84 include axial through-holes 88. Through-holes 88 may be sized such that delivery shaft 220 of insertion device 212 may axially fit and slide through through-holes 88 (FIG. 5) Holder body 86 may be angled (non-parallel) relative to axial through-holes 88 in legs 84. Holder body 86 may be generally cylindrical and include a central lumen such that it may mate or engage with an outer diameter of the handle 226 of the medical device 214. Holder body 86 may be fully open at one end such that holder body 86 may accept handle 226. Holder body 86 also include an open slot 90 on a top side of holder body 86 opposite legs 84. Open slot 90 may be sized such that shaft 228 may fit through open slot 90. Open slot 90 may also connect to a stop surface 92 at a partially closed end of holder body 86. Stop surface 92 may accommodate a distal tip of handle 226, and may stabilize the handle 226 during movement of plunger 230 in medical device 214.

As shown in FIG. 5, holder 82 may be mounted on delivery shaft 220 of insertion device 212, with delivery shaft 220 axially passing through through-holes 88 in legs 84. Medical device 214 may be positioned within holder body 86. Shaft 228 with end effector 229 is at least partially surrounded by sheath 231 and may be inserted into insertion device 214 through port 224, with or without a fitting 240, as discussed above. Shaft 228 and sheath 231 of medical device 214 may have a length such that, when secured in holder 82, distal ends of shaft 228 and sheath 231 may be positioned proximal to, flush with, or distally beyond a distal end 238 of delivery shaft 220. Then, a user may operate and deflect the insertion device 212 with one hand, with the thumb operating the deflection lever (not shown). A user may then use the thumb and middle finger of the user's other hand to hold the delivery shaft 220 between legs 84. The user may guide, orient, and/or secure the holder 82 along the outer diameter of the delivery shaft 220. The position of the holder 82 on the delivery shaft 220 may be adjusted to adjust the position of the distal ends of the shaft 228 and sheath 231 relative to the distal end 238 of the delivery shaft 220. The user may use the forefinger of the same hand to act on plunger 230 to operate the medical device 214, for example, to extend the shaft 228. The portions of the shaft 228 and sheath 231 that extend proximal to fitting 240 may determine the position of the shaft 228 and sheath 231 relative to the distal end 238 of the insertion device 212. Again, the extension of the shaft 228 by action on plunger 230 may be biased by a biasing member, and plunger 230 may include a pin and handle 226 may include a track with at least one slot to lockably position the plunger 230. It is noted that during operation of the medical device 214, a user's thumb and forefinger may be removed from the delivery shaft 220 to further maneuver the medical device 214 as discussed above.

Figure 7:
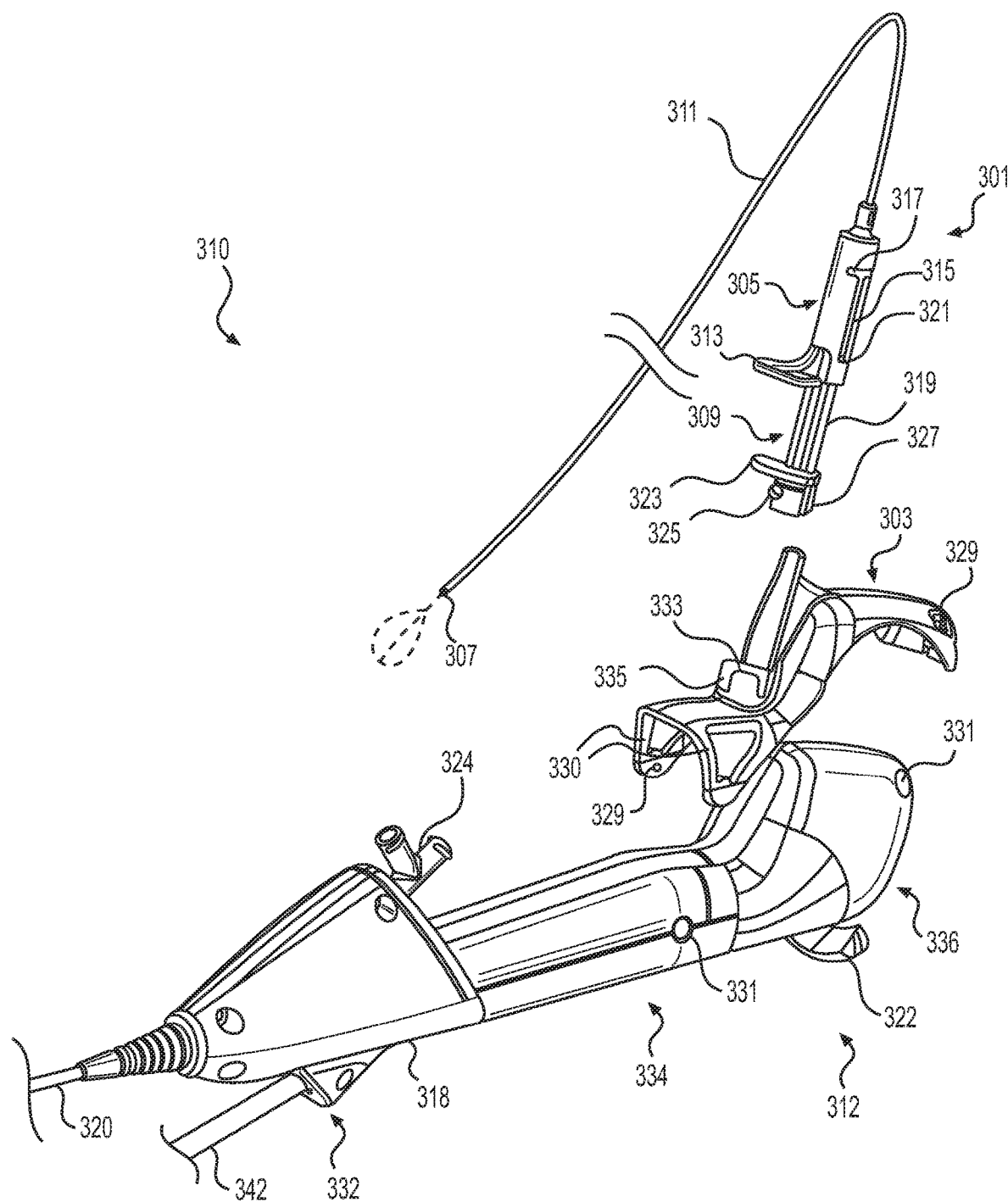
FIG. 7 illustrates a partially exploded view of a medical device, an insertion device, and an alternative holder according to aspects of this disclosure.

FIG. 7 illustrates another embodiment of this disclosure with similar elements to the medical system 10 shown by 300 added to the reference numbers. As shown, medical system 310 includes an insertion device 312 and a medical device 301 that is coupled to the insertion device 312 via a holder 303. Insertion device 312 may have a shape and functioning similar to the insertion device 12 of FIG. 1, including delivery shaft 320, deflection lever 322, port 324, and communication and power conduit 342. A fitting (not shown) may be attached to port 324 as previously discussed. A body 318 of insertion device 312 may have a distal portion 332, an intermediate portion 334, and a proximal portion 336. The intermediate portion 334 may be generally a constant diameter, and may form a portion of the insertion device 312 that a user may grip such that the user's thumb is proximate the deflection lever 322. The proximal portion 336 may be wider than the intermediate portion 334, and the deflection lever 322 may be positioned on a rounded corner of the proximal portion 336.

Medical device 301 may include a handle 305, a shaft 307, and a plunger 309. Shaft 307 may be coupled to a distal portion of plunger 309. Moreover, shaft 307 is at least partially surrounded by a sheath 311, with sheath 311 coupled to a distal portion of handle 305. Handle 305 includes an axial lumen and a trigger 313 extending laterally away from the axial lumen. Handle 305 also includes a track 315 with at least one slot 317. Handle 305 may also enclose a biasing member (not shown), such as, for example, a spiral (compression) spring, to bias the movement of plunger 309 within the axial lumen of handle 305. Plunger 309 may include an axial plunger shaft 319 with a plunger pin 321. Plunger pin 321 may be a cantilevered protrusion extending laterally away from the plunger shaft 319, and plunger pin 321 may be introduced into handle 305 via a ramp (not shown) in handle 305 that aligns with track 315. Plunger pin 321 may be positioned and movable within track 315 and lockable in slot 317. Slot 317 may extend circumferentially from track 315, and may extend in two directions from track 315. In one non-illustrated example, handle 305 may include an additional track with at least one slot, with the track and slot mirroring track 315 and slot 317 on an opposite circumferential side of handle 305. In this aspect, plunger 309 may further include an additional plunger pin to be movable and lockable within the track and slot.

Plunger 309 may further include a laterally extending trigger stop 323, which may align with trigger 313 and may aid in connecting to the holder 303. Plunger 309 may also include an alignment pin 325 and a male connector 327 such that the plunger 309, and thus medical device 301, may be coupled to insertion device 312.

Holder 303 may be coupled to insertion device 312 on an opposite side of the proximal portion 336 from the deflection lever 322. For example, holder 303 may be shaped to fit on insertion device 312 and match the contour of a portion of the intermediate portion 334 and the wider proximal portion 336. Additionally, holder 303 may include holder pins 329 at distal and proximal positions to fit, snap, or otherwise secure into indentations or holes 331 in intermediate portion 334 or proximal portion 336 of insertion device 312. In one example, holder 303 includes biased or flexible extensions 330 that connect to holder pins 329 such that the extensions 330 may bend or flex as holder pins 329 are positioned in holes 331 to couple holder 303 to insertion device 312.

Holder 303 may also include a female connector 333 and an alignment groove 335. Medical device 301 may be coupled to holder 303 by coupling male connector 327 to female connector 333. Alignment pin 325 may also be coupled into alignment groove 335 to secure plunger 309 and prevent rotation during operation.

As mentioned, when medical device 301 is coupled to insertion device 312 via holder 303, a user may operate the medical system 310 with one hand. In this example, shaft 307 may be at least partially surrounded by sheath 311, and shaft 307 and sheath 311 may have a length such that when coupled to insertion device 312, the shaft 307 and sheath 311 are flush with or just proximal or distal to distal end of the delivery shaft 320. The portions of the shaft 307 and sheath 311 that extend proximal to port 324, which may include a fitting, may determine the position of the shaft 307 and sheath 311 relative to the distal end of the insertion device 312.

The user may hold the insertion device 312 with the user's thumb proximate the deflection lever 322, such that the user's fingers wrap around the intermediate portion 334 of the insertion device 312. In this position, the user's forefinger is proximate the medical device 301, specifically trigger 313 on handle 305. A user may deflect the distal end of the delivery shaft 320 through the user's thumb acting on deflection lever 322 in order to position the distal end 338 at the target site. The user may extend the shaft 307 and sheath 311 from the distal end, and then may extend the shaft 307 out of the sheath 311 by movement of trigger 313 toward insertion device 312. If, for example, the shaft 307 includes a self-expanding retrieval basket as an end effector at a distal end, the basket may expand as the sheath 311 is retracted (shown in dashed lines in FIG. 7). Moreover, a user may lock the shaft 307 in an extended position by rotating the trigger 313 such that pin 321 on plunger shaft 319 is locked in slot 317. As discussed, slot 317 may extend in two directions circumferentially from track 315 to allow for left-handed or right-handed manipulation. Plunger 309 is secured to holder 303 via the interaction of alignment pin 325 and male connector 327 with alignment groove 335 and female connector 333. Then, a user may retract shaft 307 into sheath 311 by positioning handle 305 such that plunger pin 321 is within track 315 and removing force on trigger 313 to allow biasing member (not shown) to urge trigger 313 away from insertion device 312 to its original position. Medical device 301 may be removed from insertion device 312 to remove any captured material.

It is noted that the length of track 315 and the position and number of slot 317 may be modified depending on the shaft 307. For example, the track 315 and slot 317 shown in FIG. 7 may be used with a zero tip self-expandable retrieval basket.

Figure 8:
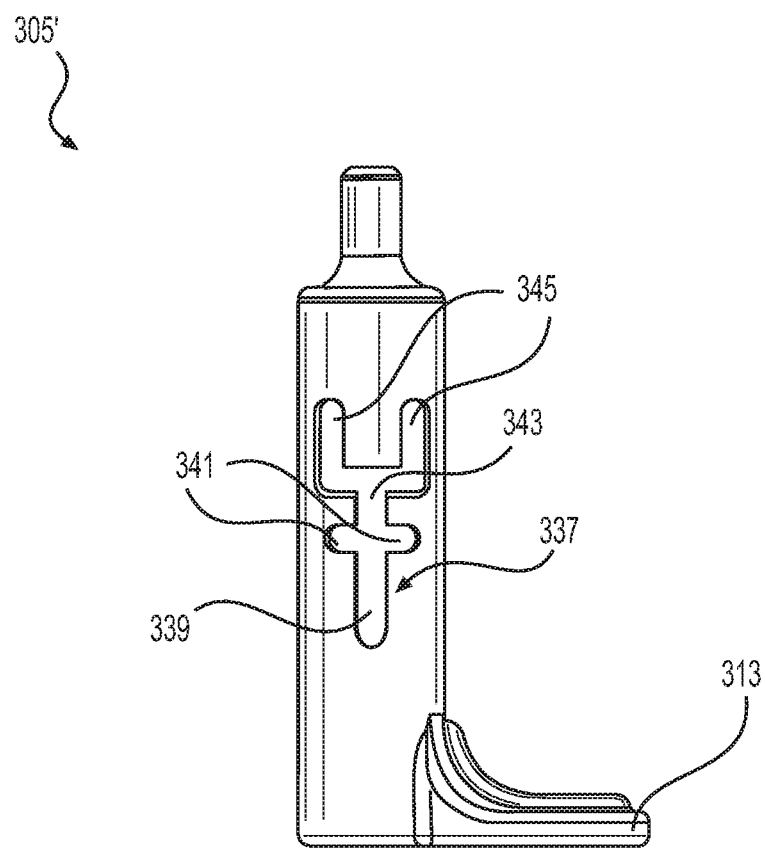
FIG. 8 illustrates an additional medical device element according to aspects of this disclosure.

FIG. 8 illustrates another embodiment of the handle 305' that may be implemented in a similar manner as discussed with respect to FIG. 7. For example, sheath 311 may be coupled to a distal portion of handle 305'. Handle 305' includes an axial lumen and a trigger 313 extending laterally away from the axial lumen. Handle 305' also includes a track 337. Track 337 may include an axially extending main slot 339 and at least two circumferentially extending tabs 341 into which plunger pin 321 may be lockably positioned. Track 337 may also include a cross slot 343 extending perpendicular to the main slot 339, as well as at least two release slots 345 extending from the cross slot 343 parallel to main slot 339. It is noted that tabs 341, cross slot 343, and release slot 345 form a mirror image for both left-handed and right-handed operation. It is also noted that handle 305' may include a same-shaped track on an opposite circumferential side of handle 305'. The length of main slot 339 forms a stroke length for trigger 313. Moreover, the positions and lengths of main slot 339, tabs 341, cross slot 343, and release slot 345 may be selected to correspond to varying positions of an end effector, such as, for example, a hybrid grasper retrieval basket, at the distal end of the shaft 307.

Figure 9:
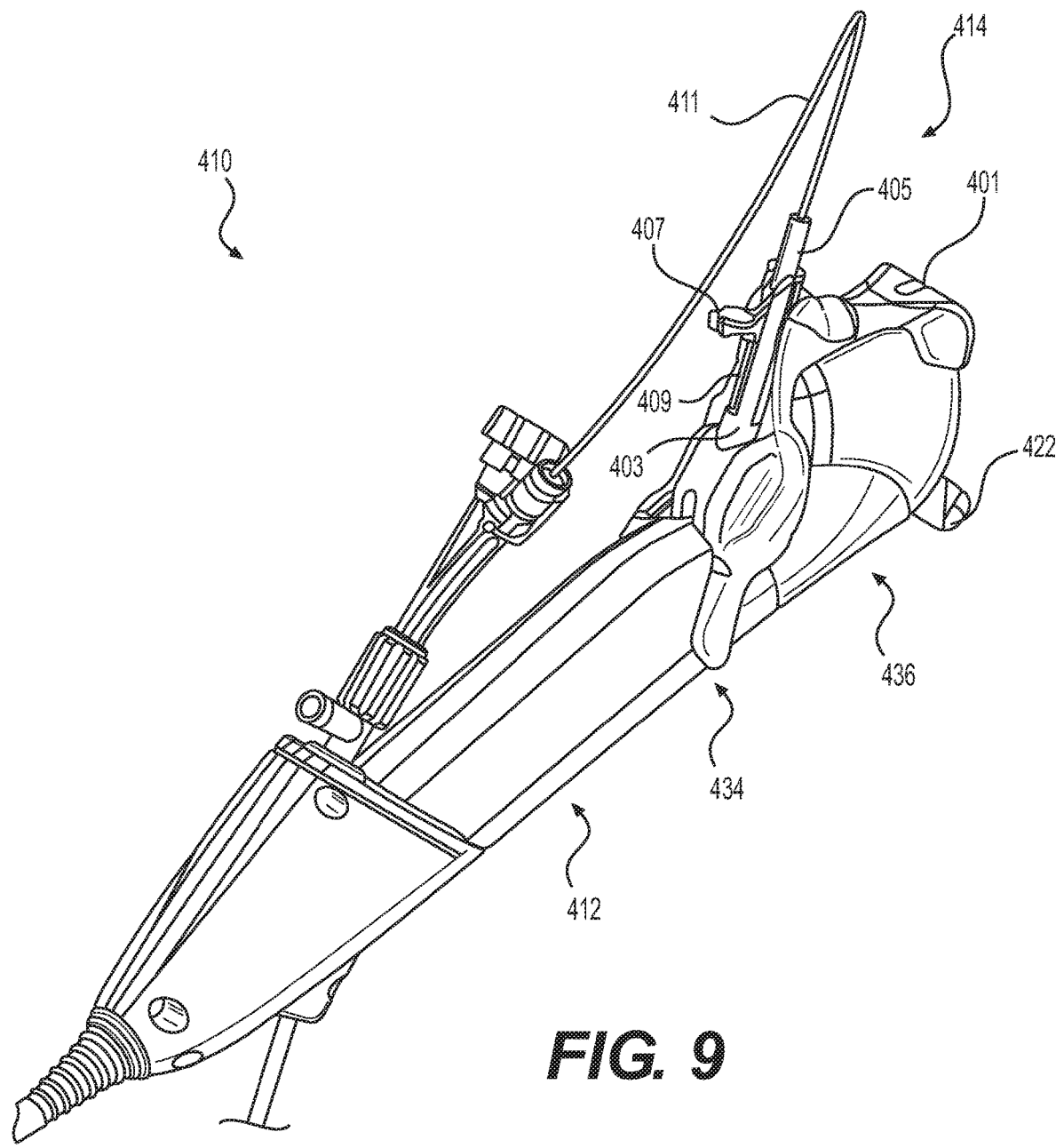
FIG. 9 illustrates a perspective view of a medical device coupled to an insertion device via an alternative holder according to aspects of this disclosure.

FIG. 9 illustrates another embodiment of this disclosure with similar elements to the medical system 10 shown by 400 added to the reference numbers. As shown, a medical system 410 includes an insertion device 412 and a medical device 414 coupled via holder 401. Insertion device 412 may operate as discussed above with respect to the other embodiments. Medical device 414 may include a slot body 403 and a plunger 405, with the movement of plunger 405 relative to slot body 403 biased by a biasing member (not shown), such as, for example, a spiral (compression) spring. Plunger 405 includes a trigger 407 laterally protruding from the plunger 405, and slot body 403 includes a main slot 409. Trigger 407 may travel through main slot 409 in order to move plunger 405 relative to slot body 403.

Holder 401 may be of a similar shape to holder 303 of FIG. 7. Holder 401 may be shaped to be fixedly coupled to an intermediate portion 434 and a proximal portion 436 of insertion device 412 such that holder 401 is positioned opposite a deflection lever 422. Holder 401 may include a female connector (not seen) on a side opposite insertion device 412 to receive slot body 403. Alternatively, slot body 403 may be integrally formed with holder 401. Although not shown, holder 401 may further include holder pins to couple holder 401 to insertion device 412 via holes, as discussed regarding FIG. 7. Holder 401 may be coupled to insertion device 412 by way of any of the aforementioned connections as well.

In this embodiment, a shaft (not seen) is at least partially surrounded by a sheath 411. The shaft may be coupled to an internal lumen in slot body 403. Sheath 411 may be coupled to an internal lumen in plunger 405. Then, action on trigger 407 through main slot 409 causes plunger 405 to move relative to slot body 403, retracting sheath 411 to extend the shaft. If the shaft includes an self-expanding retrieval basket as an end effector at a distal end, the retrieval basket may expand as the action on trigger 407 retracts sheath 411. Releasing the force on trigger 407 causes the retrieval basket to be enclosed in sheath 411.

In another non-illustrated aspect of this disclosure, slot body 403 may include tabs extending from main slot 409 such that the trigger 407 may be lockably positioned, locking the shaft in an extended position. Slot body 403 may also include a release slot as discussed above.

Figure 10:
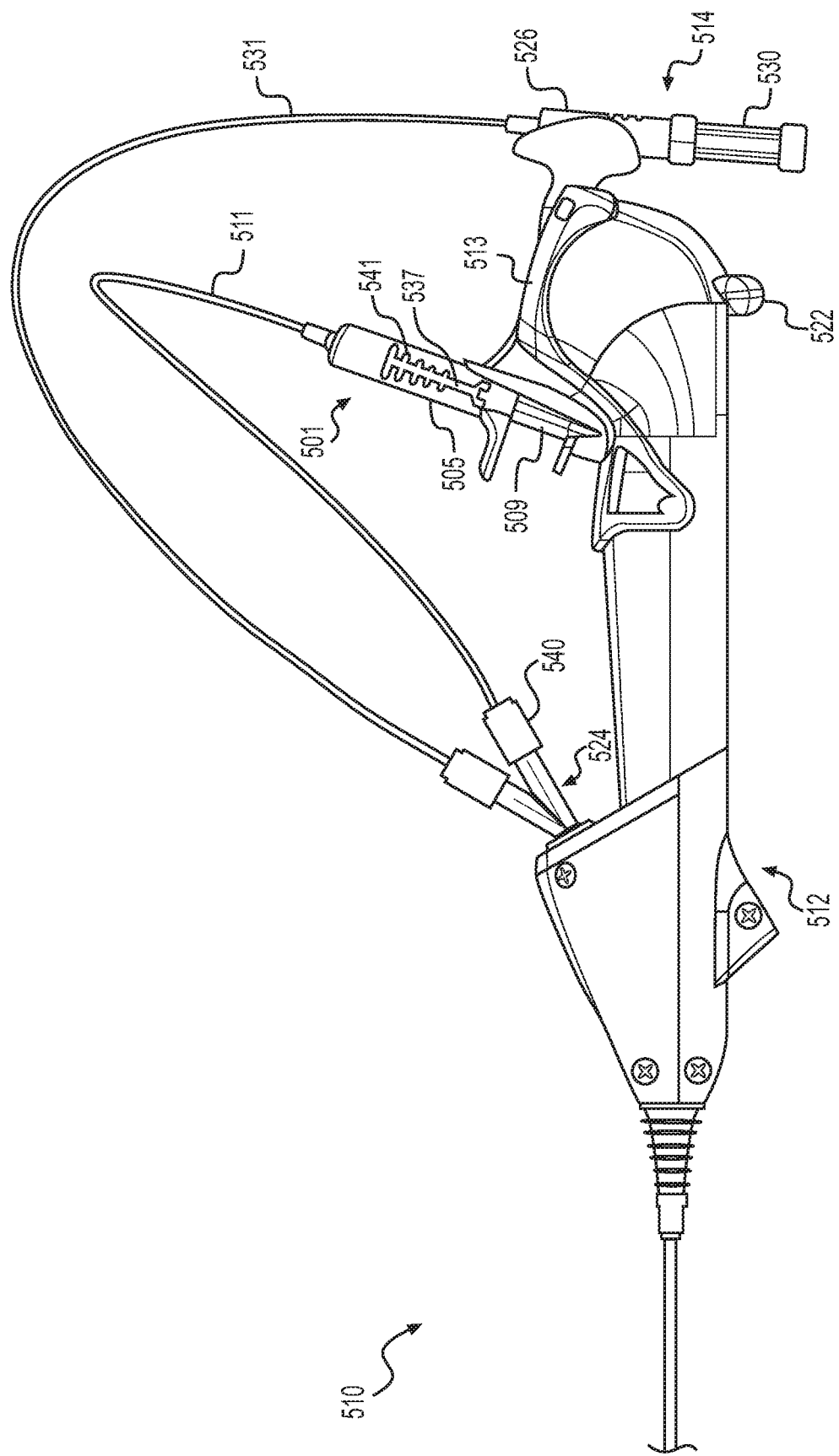
FIG. 10 illustrates two medical devices coupled to an insertion device via an alternative holder according to aspects of this disclosure.

FIG. 10 illustrates another embodiment of this disclosure with similar elements to the medical system 10 shown by 500 added to the reference numbers. As shown, a medical system 510 includes an insertion device 512 and medical devices 501 and 514 coupled to the insertion device 512 via a double holder 513 and inserted through port 524. Insertion device 512 may operate as discussed above with respect to the other embodiments. Medical device 501 may have a shape and functioning substantially similar to medical device 301, and may include a track 537 with a plurality of tabs 541 to form the arrangement shown in FIG. 10. Medical device 514 may have a shape and functioning substantially similar to medical device 14, including handle 526 and plunger 530. Double holder 513 may have a shape similar to, and may be attached to insertion device 512 as, holder 303 of FIG. 7, but with an additional protrusion that forms a portion similar to holder 16 of FIG. 1. Therefore, a user may couple two medical devices 501 and 514 to the insertion device 512.

Medical device 501 may include a handle 505, a shaft (not shown), a plunger 509, with a sheath 511 at least partially surrounding the shaft and coupled to a distal portion of handle 505. A user may also manipulate the portions of the shaft and sheath 511 that extend proximal to port 524, which may include a fitting 540, to determine the position of the shaft and sheath 511 relative to the distal end of the insertion device 512. As such, a user may position the shaft and sheath 511 relative to the distal end of the insertion device 512, and may also retract sheath 511 by action on handle 505 and plunger 509 to uncover the shaft and allow for expansion of a retrieval device. A user may lock sheath 511 in a retracted position by manipulating plunger 509 relative to handle 505 to lock a plunger pin (not shown) in one of the plurality of tabs 541 in handle 505 as discussed above.

Medical device 514 may operate as discussed with respect to medical device 14 when mounted on an insertion device in holder 16. In particular, medical device 514, when mounted via double holder 513, may be positioned proximate to deflection lever 522. A user may also manipulate the portions of the shaft and sheath 531 that extend proximal of port 524, which may include a fitting 540, to determine the position of the shaft and sheath 531 relative to the distal end of the insertion device 512. A user may extend or retract medical device 514 by action on plunger 530.

In one example, medical devices 501 and 514 may both include a retrieval basket. In another example, medical device 501 may include a retrieval basket, and medical device 514 may include a laser fiber (not shown). When medical device 514 includes a laser fiber, the laser fiber may extend proximally from the proximal end of plunger 530 in order to mate with a laser source. Alternatively, plunger 530 may include an adaptor at the proximal end to couple an additional laser fiber connected to a laser source to the laser fiber included in medical device 514.

In use, a user may deflect the distal end of insertion device 512 to be proximate to target material. A user may position one or both of the retrieval basket and laser fiber relative to the distal end of the insertion device 512 by manipulating the portions of the shafts and sheaths that extend proximal of port 524. A user may extend the laser fiber by action on plunger 530, and/or may activate the laser source to direct medical treatment to the target material through the laser fiber, for example, to break up the target material. Then, a user may extend and expand the retrieval basket included in medical device 501 by action on handle 505 and plunger 509 to capture the target material for removal.

Figure 11:
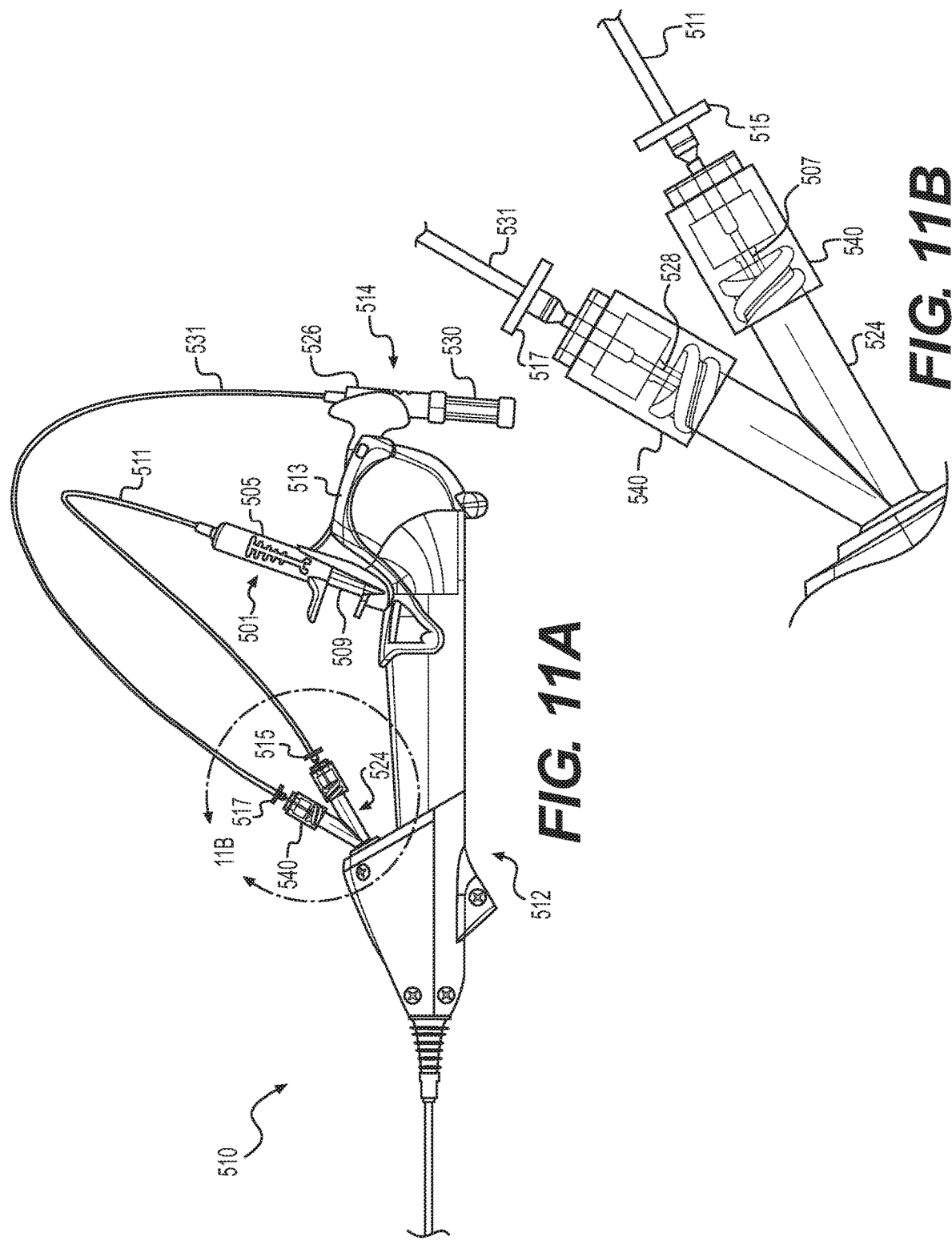
FIG. 11A illustrates two medical devices coupled to an insertion device via an alternative holder according to aspects of this disclosure.
FIG. 11B illustrates details of a portion of FIG. 11A.

FIGS. 11A and 11B illustrate a medical system similar to that of FIG. 10, where the sheaths 511 and 531 do not surround the shafts 507 and 528 of medical device 501 and 514 over the lengths of the shafts 507 and 528 that extend through insertion device 512. For example, with the medical device 501 and 514 coupled to insertion device 512 via double holder 513, sheaths 511 and 531 surround the shafts 507 and 528 from the distal ends of handles 505 and 526 to within fittings 540 (shown as semitransparent) on port 524. In this aspect, sheaths 511 and 531 may also include stops 515 and 517 that extend radially outward and are wider than the openings in fittings 540. In use, a user may adjust the position of the distal end of the insertion device 512 as discussed above. The user's manipulation of the portions of the shafts 507 and 528 and sheaths 511 and 531 that extend proximal to port 524, however, is limited by stop 515 and 517. As a result, the user may limit the extent to which shafts 507 and 528 may extend from the distal end of the insertion device 512.

For example, if shaft 528 includes a retrieval basket, the user may limit the extension of shaft 528 relative to a distal end of the insertion device 512 by locating the stop 517 on sheath 531 at the proximal end of fitting 540 on port 524. The ratios of the lengths of the shaft 528 and sheath 531 may position the retrieval basket to be flush with the distal end of the insertion device 512 in order for action on the plunger 530 relative to the medical device handle 526 to extend and expand the retrieval basket from the distal end of the insertion device 512. Alternatively, if shaft 528 includes a laser fiber, the user may use stop 517 to limit the shaft 528 to be flush with or just proximal to the distal end of the insertion device 512 in order for action on the plunger 530 relative to the medical device handle 526 to extend the laser fiber from the distal end of the insertion device 512, without the risk of the laser fiber being overextended at the surgical site. In another aspect, sheaths 511 and 531 may fully surround shafts 507 and 531 as discussed above, and may also include stops 515 and 517 to limit the extent to which shafts 507 and 528 and sheaths 511 and 531 may extend from the distal end of the insertion device 512.

Figure 12:
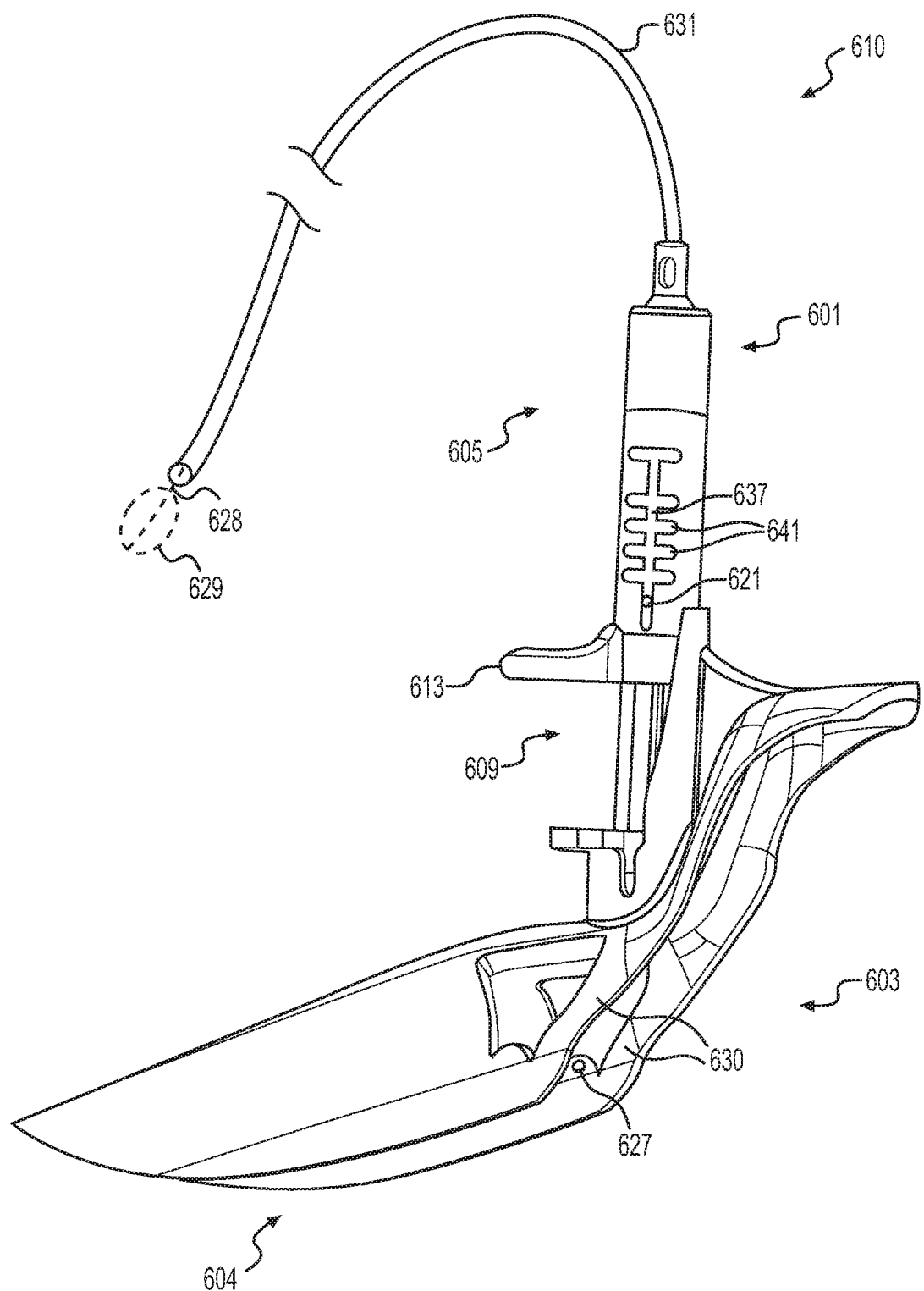
FIG. 12 illustrates a perspective view of a medical device coupled to an alternative holder according to aspects of this disclosure.

FIG. 12 illustrates a medical system 610 with a medical device 601 and holder 603 similar to the medical devices 301, 414, and 501 and holders 303, 401, and 513 of FIGS. 7-11. As shown, holder 603 may be shaped to be coupled to a proximal end of an insertion device, and may be opposite to a deflection lever, similar to that shown in FIGS. 7-11. Holder 603 also includes a distal extension 604, which may allow a user to easily hold holder 603 in the user's hand without holder 603 being attached to an insertion device. For example, distal extension 604 of holder 603 may extend generally normal to medical device 601, and may include an approximately C-shaped convex curvature with respect to medical device 601. Distal extension 604 may also have a length approximately equivalent to an intermediate portion of an insertion device, similar to intermediate portion 334 in FIG. 7, allowing a user to hold holder 603 or couple holder 603 to an insertion device.

Medical device 601 may be coupled to holder 603 as discussed with respect to medical devices 301 and 501 and holders 303 and 513 above with respect to FIGS. 7 and 10. Alternatively, medical device 601 and holder 603 may be integrally formed. Medical device 601 may function as discussed with respect to medical devices 301 and 501 above. Additionally, medical system 610 may be used separate from an insertion device. For example, a user may insert medical device 601 to a target site and may hold holder 603 like a pistol with distal extension 604 in a user's hand and the user's forefinger in proximity to trigger 613. Then, through action on trigger 613 of handle 605 relative to plunger 609, the user may extend shaft 628 from sheath 631 to expand end effector 629. The user may lockably position shaft 628 relative to sheath 631 by positioning plunger pin 621 in tabs 641 in track 637.

Moreover, medical system 610 may be coupled to an insertion device with holder 603 including holder pins 627 to fit, snap, or otherwise secure into indentations or holes in a portion of an insertion device as discussed above with respect to FIG. 7. In one example, holder 603 includes biased or flexible extensions 630 that connect to holder pins 627 such that the extensions 630 may bend or flex as holder pins 627 are positioned in the holes in the insertion device to couple holder 603 to an insertion device. As such, medical system 610 may be used as a stand alone device or may be coupled to and inserted through an insertion device as discussed above.

The disclosed holders (16, 70, 82, 303, 401, 513, and 603) coupling the medical devices to the insertion devices may help enable quick and reliable performance of a medical procedure such as, for example, the capture and removal of a stone or material. For example, a user may couple an existing medical device to an existing insertion device with one of the disclosed holders, without the need for new specialized medical equipment. Then, the user may be able to manipulate both the distal end of the insertion device and the extension and/or rotation of the shaft of the medical device with one or two hands. Additionally, with the medical device coupled to the insertion device via one of the aforementioned holders, the user may lockably position the shaft of the medical device while deflecting the distal end of the insertion device or performing other medical treatments. This allows the user to perform other steps with the user's other hand, and also reduces the number of users and time necessary for the performance of the medical treatment.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. An insertion device, comprising:
 a body and a delivery shaft,
  wherein the body includes a longitudinal axis aligned with a central long axis of a proximal end of the delivery shaft; and
 a holder coupled to the body of the insertion device,
  wherein the holder includes a medical device receiving chamber having a longitudinal axis that is non-parallel to the longitudinal axis of the body,
  wherein the medical device receiving chamber has a semi-circular shape and is located at a top portion of the holder,
  wherein the holder further includes a stop surface forming an extension of the medical device receiving chamber, wherein the stop surface has a semi-circular shape that is aligned with the semi-circular shape of the receiving chamber, and
  wherein the stop surface is narrower and/or shallower than the medical device receiving chamber.

2. The insertion device of claim 1, further including an attachment surface.

3. The insertion device of claim 2, wherein the holder further includes a finger ridge opposite the attachment surface.

4. The insertion device of claim 2, wherein the attachment surface is coupled to a rounded portion of the body.

5. The insertion device of claim 2, wherein the attachment surface includes slots, shallow grooves, or projections.

6. The insertion device of claim 1, wherein the insertion device further includes a deflection lever to deflect a distal end of the delivery shaft; and
 wherein the holder is coupled to a proximal portion of the body of the insertion device on a side opposite to the deflection lever.

7. The insertion device of claim 1, further comprising a medical device coupled to the insertion device via the holder,
 wherein the medical device includes a shaft, and the shaft is introduced into the delivery shaft.

8. The insertion device of claim 1, wherein the body of the insertion device includes holes, and the holder further includes a distal extension and holder pins to fit within the insertion device holes and assist in coupling the holder to the insertion device.

9. The insertion device of claim 1, further comprising a medical device coupled to the insertion device via the holder.

10. An insertion device, comprising:
 a body and a delivery shaft extending from the body; and
 a medical device holder coupled to one of the body or the delivery shaft, the medical device holder including:
  a handle chamber; and
  a stop surface having an edge facing the handle chamber,
   wherein the handle chamber has a longitudinal axis that is non-parallel to the longitudinal axis of the body,
   wherein the handle chamber has a semi-circular shape and is located at a top portion of the medical device holder,
  wherein the stop surface is formed by an extension of the handle chamber, wherein the stop surface has a semi-circular shape that is aligned with the semi-circular shape of the handle chamber, and
  wherein the stop surface is narrower and/or shallower than the handle chamber.

11. The insertion device of claim 10, wherein the medical device holder further includes an attachment surface; and
 wherein the attachment surface is coupled to a proximal portion of the body.

12. An insertion device, comprising:
 a body having a distal portion, an intermediate portion, and a proximal portion;
 a delivery shaft extending from the distal portion;
 a deflection lever on the proximal portion to deflect a distal end of the delivery shaft; and
 a medical device holder coupled to the proximal portion,
  wherein the medical device holder includes a medical device receiving chamber having a longitudinal axis that is non-parallel to the longitudinal axis of the body,
  wherein the medical device receiving chamber has a semi-circular shape and is located at a top portion of the medical device holder, wherein the medical device holder further includes a stop surface forming an extension of the medical device receiving chamber, wherein the stop surface has a semi-circular shape that is aligned with the semi-circular shape of the medical device receiving chamber, and wherein the stop surface is narrower and/or shallower than the medical device receiving chamber.

13. The insertion device of claim 12, wherein the medical device holder is coupled to the proximal portion of the body on a side opposite the deflection lever; and wherein the medical device holder is configured to simultaneously couple two medical devices to the body of the insertion device.

14. The insertion device of claim 13, further comprising at least one medical device coupled to the medical device holder;

wherein one of the at least one medical device includes a handle, a plunger, and a shaft coupled to a distal end of the plunger.

* * * * *